United States Patent [19]

Bachman

[11] 4,348,317

[45] Sep. 7, 1982

[54] RECOVERY OF L-PHENYLALANINE AND L-ASPARTIC ACID DURING PREPARATION OF α-L-ASPARTYL-L-PHENYLALANINE METHYL ESTER

[75] Inventor: Gerald L. Bachman, Des Peres, Mo.

[73] Assignee: Monsanto Company, St. Louis, Mo.

[21] Appl. No.: 221,128

[22] Filed: Dec. 29, 1980

[51] Int. Cl.$^3$ .................... C07C 99/12; C07C 103/52
[52] U.S. Cl. ............................ 260/112.5 R; 562/443; 562/571
[58] Field of Search .............................. 562/443, 571; 260/112.5 R

[56] References Cited

U.S. PATENT DOCUMENTS

| | | | |
|---|---|---|---|
| 3,030,380 | 4/1962 | Weygand et al. | 562/443 |
| 3,493,602 | 2/1970 | Suranyi et al. | 562/443 |
| 4,173,562 | 11/1979 | Bachman et al. | 260/112.5 R |

FOREIGN PATENT DOCUMENTS

| | | | |
|---|---|---|---|
| 607956 | 11/1960 | United Kingdom | 562/571 |
| 191574 | 1/1967 | U.S.S.R. | 562/571 |

OTHER PUBLICATIONS

Handbook of Chem. & Phys. 60 Edn., p. C-757 (1979).

*Primary Examiner*—Natalie Trousof
*Assistant Examiner*—James H. Reamer
*Attorney, Agent, or Firm*—Robert E. Wexler; Howard C. Stanley

[57] ABSTRACT

There is described an improved process for the separation and recovery of L-phenylalanine and L-aspartic acid from sidestreams resulting from the preparation of α-L-aspartyl-L-phenylalanine methyl ester. It has been found that superior separation is obtained by combining one or more of the mother liquor and wash solutions formed during the preparation of α-L-aspartyl-L-phenylalanine methyl ester, hydrolyzing same to afford the hydrohalide salts of L-aspartic acid and L-phenylalanine, acidifying the hydrolysis solution to precipitate the hydrohalide salt of L-phenylalanine, separating the hydrohalide salt of L-phenylalanine, dissolving it in water and adjusting the pH of the solution to the isoelectric point of L-phenylalanine, thus affording pure L-phenylalanine, and thereafter adjusting the pH of the solution after separation of the L-phenylalanine hydrohalide to the isoelectric point of L-aspartic acid to precipitate L-aspartic acid.

20 Claims, No Drawings

RECOVERY OF L-PHENYLALANINE AND L-ASPARTIC ACID DURING PREPARATION OF α-L-ASPARTYL-L-PHENYLALANINE METHYL ESTER

BACKGROUND OF THE INVENTION

This invention relates to a process for the preparation of α-L-aspartyl-L-phenylalanine methyl ester (α-APM). α-APM is well known for its usefulness as a sweetening agent.

Synthesis of α-APM, according to a previous invention of U.S. Pat. No. 4,173,562, proceeds by the reaction of an N-protected L-aspartic anhydride and L-phenylalanine to afford N-protected α-L-aspartyl-L-phenylalanine. The protecting group which is used to shield the nitrogen of the amino group of the aspartic acid may be any of those known to persons skilled in the art, as exemplified by formyl, acetyl, benzoyl, substituted and unsubstituted carbobenzoxy, t-butoxycarbonyl, hydrohalide salt and the like. Particularly preferred is the formyl group. Thus, N-formyl-L-aspartic anhydride (FAA) is the preferred material which is coupled with L-phenylalanine to afford N-formyl-α-L-aspartyl-L-phenylalanine (FAP). In the reaction of FAA and phenylalanine to afford FAP, both the α- and β-isomers of FAP are obtained. The α-isomer is then separated from the mixture of isomers and the α-FAP thus-obtained is treated to remove the protecting group. As set forth in our U.S. patent described above, any method suitable for removing the protecting groups from amines is appropriate.

After removal of the protecting group, the α-L-aspartyl-L-phenylalanine (α-AP) is esterified in methanolic hydrogen chloride to afford the hydrochloride salt of the methyl ester of α-L-aspartyl-L-phenylalanine (α-AMP.HCl). The α-APM.HCl is then neutralized with aqueous caustic to afford α-L-aspartyl-L-phenylalanine methyl ester (α-APM).

In Japanese patent publication 8097812, assigned to Teijin, Ltd., a two-step process for recovering amino acids is disclosed wherein the mother liquor from the coupling of a blocked aspartic anhydride and the methyl ester of L-phenylalanine was hydrolyzed with aqueous mineral acid and the pH of the solution was adjusted to pH 6 to precipitate L-phenylalanine and then to pH 2 to precipitate L-aspartic acid. In this publication, however, the recovery procedure is concerned with recovering amino acids from a completely different mother liquor than that which is utilized by the present invention.

In the publication described above, only the mother liquor from the initial coupling step is used as a source for recovery of L-phenylalanine and L-aspartic acid. Further, the procedure involves only the two-step precipitation of amino acids from the hydrolysis solution. It has been discovered that direct application of the two-step separation process of the Japanese publication to the reaction mixtures of the present invention does not afford amino acids of as high purity as the process of the present invention.

SUMMARY OF THE INVENTION

It has now been found that superior recovery of L-aspartic acid and L-phenylalanine is afforded by a procedure which may be applied to one or more of the sidestreams resulting from the preparation of α-APM. Thus, instead of recovering L-aspartic acid and L-phenylalanine only from the coupling reaction mother liquor as was done heretofore, and then only by direct precipitation from such mother liquor, the present invention contemplates recovery from a different coupling reaction mother liquor alone or in combination with one or more of the following sidestreams resulting from the process for preparing α-APM as disclosed in U.S. Pat. No. 4,173,562:

Esterification mother liquor
α-APM mother liquor
α-FAP wash
α-APM.HCl wash
α-APM wash The procedure used to recover L-aspartic acid and L-phenylalanine from one or more of the above streams comprises, in general, concentration of the mother liquor or wash, distillation, acidification, neutralization and adjustment of pH to the appropriate amino acid isoelectric point to recover the desired amino acid.

Although the above procedure affords a more complete recovery of the amino acids from the sidestreams resulting from the preparation of α-APM, the critical point of the invention occurs at the last stage of the described procedure wherein the amino acids are separated in three steps. Thus, instead of directly precipitating L-phenylalanine, L-phenylalanine hydrochloride is initially separated. It is then dissolved and converted to L-phenylalanine and the solution which remains after precipitation of the L-phenylalanine hydrochloride is treated to afford L-aspartic acid. By initially separating L-phenylalanine as its salt, it is removed more cleanly and completely than known heretofore where L-phenylalanine is recovered directly from solution.

Accordingly, the essence of the invention is directed to a process for recovering L-phenylalanine and L-aspartic acid from at least one sidestream resulting from the preparation of α-APM which comprises concentrating one or more sidestreams, subjecting the sidestream to concentration, distillation and hydrolysis and distillation procedures and finally acidifying the treated sidestream with a concentrated mineral acid, such as hydrochloric acid or hydrobromic acid, to effect hydrolysis to convert the available L-phenylalanine and L-aspartic acid to the salt form. Upon further acidification, the salt of L-phenylalanine separates from the solution. It is then redissolved in water and the pH of the solution is adjusted to the isoelectric point of L-phenylalanine to afford pure L-phenylalanine. The acidified solution from which the salt of L-phenylalanine separated is then neutralized and the pH is adjusted to the isoelectric point of L-aspartic acid to afford L-aspartic acid.

PREFERRED EMBODIMENTS OF THE INVENTION

As set forth above, superior recovery of L-aspartic acid and L-phenylalanine is afforded by the procedure outlined below which may be applied to the coupling reaction mother liquor alone or in combination with one or more of the sidestreams resulting from the preparation of α-APM.

Thus, L-aspartic acid and L-phenylalanine may be recovered from the mother liquor remaining after the coupling reaction and subsequent separation of α-FAP from the coupling reaction mixture. Such mother liquor contains α- and β-FAP, formyl aspartic acid, acetic acid and formic acid. Also, L-phenylalanine and L-aspartic acid may be recovered from the mother liquor remaining after the esterification reaction wherein α-AP is converted to α-APM.HCl. Such mother liquor contains α-APM.HCl which didn't crystallize, α-AP.HCl, water, methanol, methyl formate, formic acid and the hydrochloride salt of the byproduct ester and diester referred to in U.S. Pat. No. 4,173,562. Further, the amino acid values may be recovered from the α-APM mother liquor remaining after separation of the α-APM. Such mother liquor contains α-APM, α-AP, water, the byproduct ester and diester referred to above and NaCl.

In addition to the mother liquors resulting from the coupling, esterification and neutralization steps, described above, L-aspartic acid and L-phenylalanine are available as derivatives thereof in the various wash liquors utilized in the process of U.S. Pat. No. 4,173,562. Thus, the α-FAP wash contain α-FAP and acetic acid. The α-APM.HCl wash contains water, α-AP.HCl, α-APM.HCl and the hydrochloride salts of the aforementioned byproduct ester and diester. The α-APM wash contains α-APM, α-AP, the aforementioned ester and diester and NaCl.

According to the invention, one or more of the sidestreams discussed above may be treating in conjunction with the coupling reaction mother liquor in the following manner:
1. The mother liquor or wash liquor is concentrated;
2. The liquor is distilled to remove low boiling impurities, if present (this step is usually only necessary when dealing with the coupling and esterification mother liquors);
3. The concentrated liquor is hydrolyzed with aqueous mineral acid to afford the inorganic salts of L-aspartic acid and L-phenylalanine;
4. The liquor is acidified to precipitate the inorganic salt of L-phenylalanine and the precipitate is recovered and dissolved in water;
5. The solution is neutralized and the pH is adjusted to the isoelectric point of L-phenylalanine which is recovered; and
6. The solution remaining after removal of the L-phenylalanine salt is neutralized and the pH is adjusted to the isoelectric point of L-aspartic acid which is recovered.

The procedure described above affords L-aspartic acid and L-phenylalanine which may be recycled without further purification to earlier stages of the α-APM process.

In accordance with U.S. Pat. No. 4,173,562, a slurry of FAA in acetic acid is coupled with crystalline L-phenylalanine to afford a reaction mixture containing α- and β-FAP. The reaction mixture is centrifuged to remove α-FAP and the α-FAP cake is washed with acetic acid and dried.

To the α-FAP cake in a hydrolyzer there is charged water, 35% hydrochloric acid and methanol. The solution is heated to complete the hydrolysis and esterification of α-FAP to α-AP and, ultimately, to α-APM.HCl.

In accord with the present invention, the coupling reaction mixture is centrifuged to recover α-FAP and the mother liquor is held for subsequent recovery of amino acids.

The α-FAP is washed with acetic acid and the wash solution is held for subsequent recovery of amino acids.

The α-FAP is then hydrolyzed and esterified with methanolic hydrogen chloride to afford α-APM.HCl.

The α-APM.HCl is separated and the mother liquor is held for recovery of amino acids.

The α-APM.HCl is washed with water and the wash solution is held for amino acid recovery.

The α-APM.HCl is neutralized with caustic to afford α-APM which is separated and recovered. The α-APM mother liquor is held for recovery of amino acids.

The α-APM is washed with water and the wash solution is held for recovery of amino acids.

Any one or more of the mother liquors and wash solutions described above may be combined with the coupling reaction mother liquor and treated in accordance with the invention to recover L-aspartic acid and L-phenylalanine.

Thus, the coupling reaction mother liquor stream is charged to a still where the batch is concentrated to about 45–100% solids content by heating at about 45° to about 80° C., preferably about 50°–60° C. The contents of the still may then be combined with one or more of the above-described streams and transferred to a hydrolyzer to which is added a concentrated mineral acid, i.e., 35% hydrochloric acid in water. The temperature is raised to hydrolysis temperature, i.e., about 105° C., and low boiling impurities are distilled and removed, e.g., methyl acetate, methyl formate, formic acid, acetic acid, methanol and water. Hydrolysis conditions are maintained for 10–15 hours to assure complete reaction.

The batch is then charged to a crystallizer and additional concentrated mineral acid, i.e., 35% hydrochloric acid, is added to afford a strongly acidic solution from which L-phenylalanine hydrochloride may be separated. The crude, wet L-phenylalanine hydrochloride recovered is dissolved in water, neutralized and the pH of the solution is adjusted to the appropriate isoelectric point with caustic to afford pure L-phenylalanine. The solution remaining after centrifugation of the L-phenylalanine hydrochloride is then neutralized with caustic and the pH is adjusted to the appropriate isoelectric point to afford L-aspartic acid which separates and is recovered by centrifugation.

EXAMPLE I

To a slurry of 1.32 moles FAA in acetic acid, there were charged 1.26 moles of L-phenylalanine. The slurry was stirred at 50° C. for one-fourth hour and cooled to 23° C. to afford a mixture of α- and β-FAP. The α-FAP was removed by centrifugation and washed with acetic acid. The mother liquor and the acetic acid wash were held for subsequent recovery of amino acid values.

EXAMPLE II

To a hydrolyzer there were charged 0.68 mole of 35% hydrochloric acid, 2.75 moles of methanol and the mixture was heated to 50° C. There was then charged 0.59 mole α-FAP. The mixture was then heated to 60° and held until hydrolysis of the α-FAP to α-AP was completed.

To the hydrolyzer there were then charged 1.32 moles of 35% hydrochloric acid at 30° C. The mixture was stirred to afford α-APM.HCl. The α-APM.HCl was centrifuged off and washed with water. The mother liquor was held for recovery of amino acids.

EXAMPLE III

This Example illustrates the recovery procedure of the present invention.

To a still there were charged the mother liquor and acetic acid wash of Example I and the mixture was concentrated to 45% solids at 55° C. The contents of the still were then transferred to a hydrolyzer and combined with the mother liquor of Example II and there were added 0.50 mole HCl and 1.60 moles water. The mixture was then heated to 105° C. with stirring while low boilers were removed. The solution was held at 105° C. for 13 hours to effect hydrolysis. The mixture was transferred to a crystallizer where the temperature was adjusted to 80° C. and 3.27 moles of HCl were added. The mixture was then cooled to 50° C. over 3 hours and then adjusted to 5° C. L-phenylalanine hydrochloride was then centrifuged from the mixture. To the L-phenylalanine hydrochloride dissolved in 157.6 g. of deionized water was added 0.66 mole sodium hydroxide in order to adjust the pH of the solution to the isoelectric point (pH 5.0). At the isoelectric point there was afforded a 61% yield of available L-phenylalanine.

The mother liquor remaining after the centrifugation of the L-phenylalanine hydrochloride was adjusted with sodium hydroxide to the isoelectric point of L-aspartic acid (pH 2.8) to afford 50% yield of available L-aspartic acid.

The L-phenylalanine and L-aspartic acid are separated cleanly by the above method and are of sufficient purity to be used, without further purification, in the preparation of α-APM.

What is claimed is:

1. In a process for preparing α-APM comprising reacting an N-protected-L-aspartic anhydride and L-phenylalanine to form the α- and β-isomers of N-protected L-aspartyl-L-phenylalanine, separating α-L-aspartyl-l-phenylalanine, removing the N-protecting group to afford α-L-aspartyl-L-phenylalanine, esterifying said α-L-aspartyl-L-phenylalanine in aqueous, methanolic hydrogen halide to afford a precipitate of the hydrogen halide salt of α-APM and neutralizing said hydrogen halide salt of α-APM to afford α-APM, said process including separation and washing steps resulting in sidestreams, the improvement comprising recovering L-phenylalanine and L-aspartic acid from at least one of said sidestreams by a process comprising acidifying said sidestream to afford a first solution containing L-aspartic acid and a salt of L-phenylalanine and from which solution the salt of L-phenylalanine precipitates and is removed, forming a second solution by dissolving said removed salt of L-phenylalanine in a solvent therefor and adjusting the pH of said second solution to precipitate L-phenylalanine and adjusting the pH of said first solution to precipitate L-aspartic acid.

2. Process of claim 1 wherein acidification is accomplished with a mineral acid.

3. Process of claim 2 wherein said acid is hydrochloric acid.

4. Process of claim 1 wherein said solvent is hydrochloric acid.

5. In a process for preparing α-APM comprising reacting an N-protected-L-aspartic anhydride and L-phenylalanine to form the α- and β-isomers of N-protected L-aspartyl-L-phenylalanine, separating α-L-aspartyl-L-phenylalanine, removing the N-protecting group to afford α-L-aspartyl-L-phenylalanine, esterifying said α-L-aspartyl-L-phenylalanine in aqueous, methanolic hydrogen halide to afford a precipitate of the hydrogen halide salt of α-APM and neutralizing said hydrogen halide salt of α-APM to afford α-APM, said process including separation and washing steps resulting in sidestreams, the improvement comprising recovering L-phenylalanine and L-aspartic acid from at least one of said sidestreams by a process comprising concentrating said sidestream, optionally distilling said sidestream to remove low boiling impurities if present, hydrolyzing and acidifying said sidestream to afford a first solution containing L-aspartic acid and a salt of L-phenylalanine, recovering said salt of L-phenylalanine from said first solution, forming a second solution by dissolving said salt of L-phenylalanine in a solvent therefor and adjusting the pH of said second solution to the isoelectric point of L-phenylalanine whereby L-phenylalanine is recovered, and adjusting the pH of said first solution to the isoelectric point of L-aspartic acid whereby L-aspartic acid is recovered.

6. Process of claim 5 wherein said sidestream is the mother liquor resulting from the coupling reaction of formyl-L-aspartic anhydride and L-phenylalanine and is concentrated to about 45–100% solids.

7. Process of claim 5 wherein said salt is the hydrochloride salt.

8. Process of claim 5 wherein said hydrolysis is conducted at about 105° C.

9. Process of claim 5 wherein said concentration is conducted at about 50°–60° C.

10. Process of claim 5 wherein acidification is accomplished with aqueous 35% hydrochloric acid.

11. Process of claim 1 wherein said sidestream is the mother liquor resulting from the esterification of α-AP to the hydrogen halide salt of α-APM.

12. Process of claim 1 wherein said sidestream is the mother liquor resulting after separation of α-APM.

13. Process of claim 1 wherein said sidestream is the wash liquor remaining after washing the α-AP containing a nitrogen-protecting group.

14. Process of claim 1 wherein said sidestream is the wash liquor from the α-APM hydrogen halide wash.

15. Process of claim 1 wherein said sidestream is the α-APM wash liquor.

16. Process of claim 5 wherein said sidestream is the mother liquor resulting from the esterification of α-AP to the hydrogen halide salt of α-APM.

17. Process of claim 5 wherein said sidestream is the mother liquor resulting after separation of α-APM.

18. Process of claim 5 wherein said sidestream is the wash liquor remaining after washing the α-AP containing a nitrogen-protecting group.

19. Process of claim 5 wherein said sidestream is the wash liquor from the α-APM hydrogen halide wash.

20. Process of claim 5 wherein said sidestream is the α-APM wash liquor.

* * * * *

UNITED STATES PATENT AND TRADEMARK OFFICE
CERTIFICATE OF CORRECTION

PATENT NO. : 4,348,317
DATED : September 7, 1982
INVENTOR(S) : Gerald L. Bachman It is certified that error appears in the above-identified patent and that said Letters Patent are hereby corrected as shown below:

Column 5, Claim 4, lines 55-56, "hydrochloric acid" should read --water--.

Column 5, line 32, "aspartyl-l-phenylalanine," should read --aspartyl-L-phenylalanine,--.

Column 1, lines 37-38, and each occurrence thereafter throughout the Letters Patent, "α-AMP.HCl" should read --α-AMP·HCl--.

Signed and Sealed this

Twenty-eighth Day of June 1983

[SEAL]

Attest:

GERALD J. MOSSINGHOFF

Attesting Officer

Commissioner of Patents and Trademarks